United States Patent
Eich et al.

(10) Patent No.: US 8,398,593 B2
(45) Date of Patent: Mar. 19, 2013

(54) BRAKE FOR INJECTION DEVICES

(75) Inventors: Adrian Eich, Wangenried (CH); Aurèle Horisberger, Allschwil (CH); Patrick Hostettler, Hasle-Rüegsau (CH); Malte Kladiwa, Bern (CH); Stefan Meier, Aarberg (CH); Peter Stettler, Kirchberg (CH); Jürgen Wittmann, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 67 days.

(21) Appl. No.: 12/869,282

(22) Filed: Aug. 26, 2010

(65) Prior Publication Data

US 2011/0077595 A1 Mar. 31, 2011

Related U.S. Application Data

(63) Continuation of application No. PCT/CH2009/000077, filed on Feb. 26, 2009.

(30) Foreign Application Priority Data

Feb. 29, 2008 (DE) .......................... 10 2008 011 881

(51) Int. Cl.
*A61M 5/20* (2006.01)

(52) U.S. Cl. .............................. 604/135; 604/131; 604/68
(58) Field of Classification Search .................. 604/131, 604/134, 135, 151, 154, 208–211, 68
See application file for complete search history.

(56) References Cited

U.S. PATENT DOCUMENTS

| 4,874,381 | A | * | 10/1989 | Vetter ........................... 604/191 |
| 5,320,609 | A | | 6/1994 | Haber et al. |
| 5,584,815 | A | * | 12/1996 | Pawelka et al. ............... 604/191 |
| 2009/0254035 | A1 | | 10/2009 | Kohlbrenner et al. |

FOREIGN PATENT DOCUMENTS

| DE | 0 426 587 | 3/1926 |
| DE | 100 15 615 | 10/2001 |
| EP | 0 525 525 | 2/1993 |
| WO | WO 00/24441 | 5/2000 |
| WO | WO 03/011370 | 2/2003 |
| WO | WO 03/092771 | 11/2003 |
| WO | WO 2008/031239 | 3/2008 |
| WO | WO 2008/053243 | 5/2008 |
| WO | WO 2008/112472 | 9/2008 |

\* cited by examiner

*Primary Examiner* — Laura Bouchelle
(74) *Attorney, Agent, or Firm* — Dorsey & Whitney LLP; David E. Bruhn, Esq.

(57) ABSTRACT

A brake mechanism for an injection device for generating a braking action on a moving, e.g. rotating, part or component of the injection device.

14 Claims, 11 Drawing Sheets

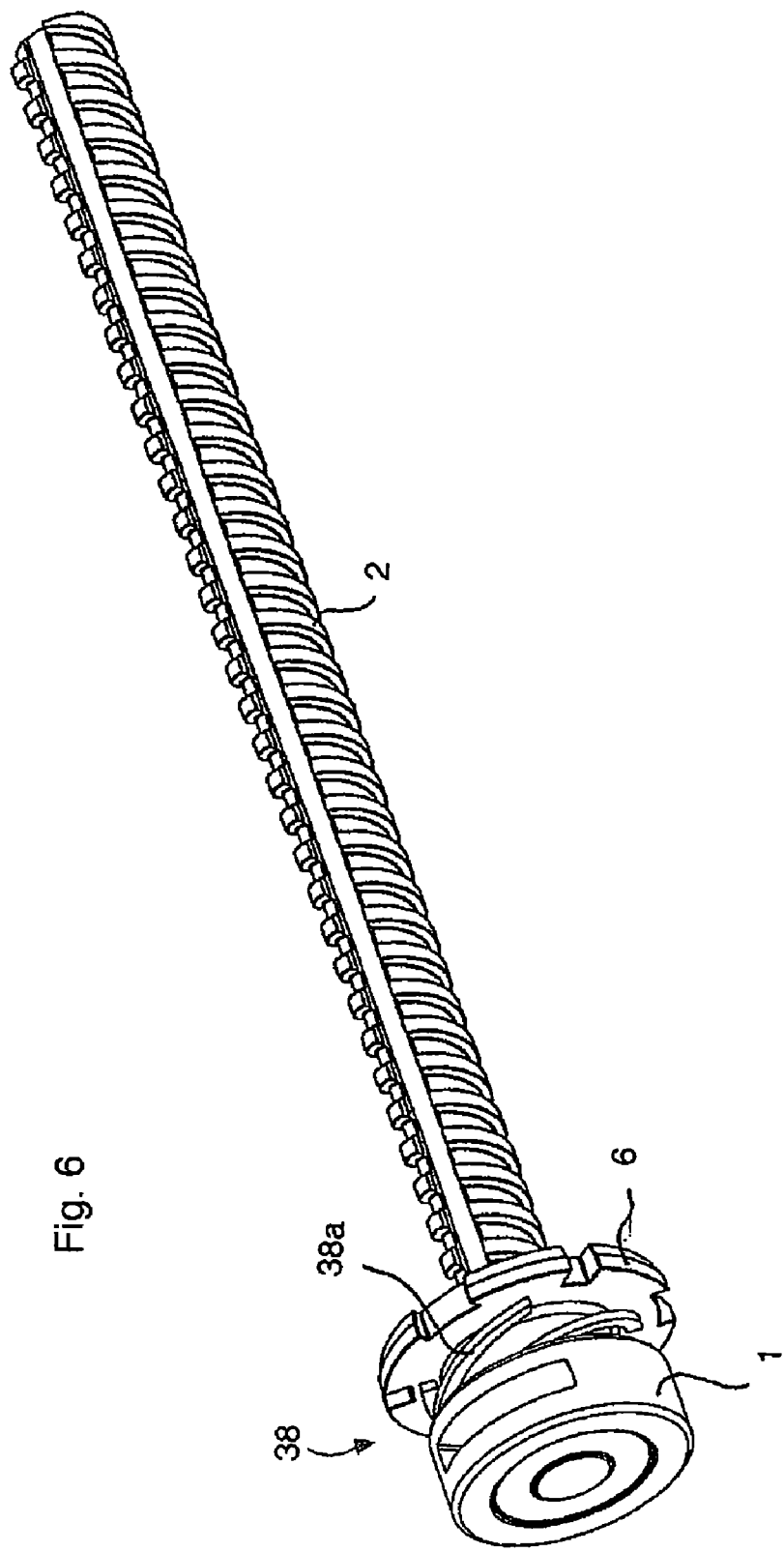

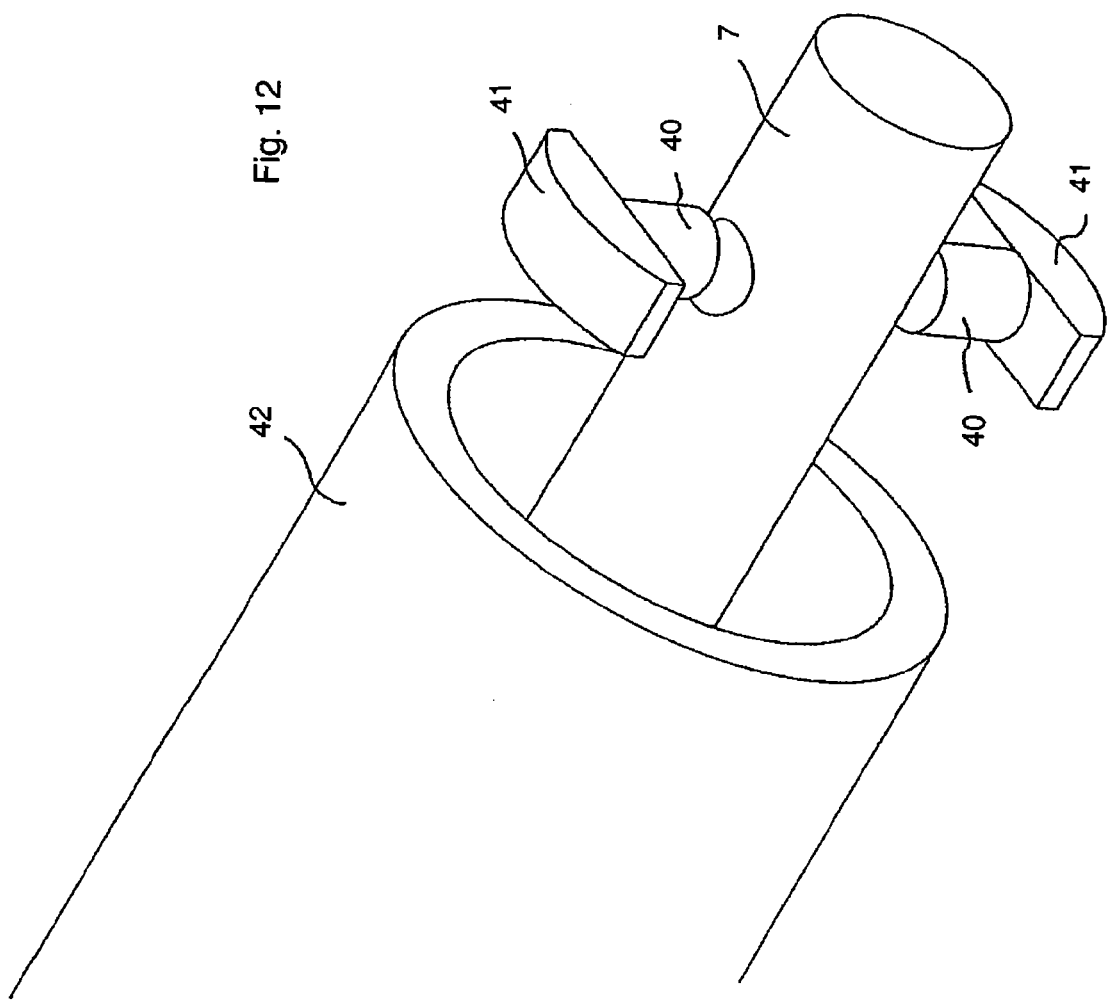

BRAKE FOR INJECTION DEVICES

CROSS-REFERENCED RELATED APPLICATIONS

This application is a continuation of International Patent Application No. PCT/CH2009/000077 filed Feb. 26, 2009, which claims priority to German Patent Application No. 10 2008 011 881.8 filed Feb. 29, 2008, the entire contents of each of which are incorporated herein by reference.

BACKGROUND

The present invention relates to devices for injecting, delivering, administering, infusing or dispensing a substance or product, and to methods of making and using such devices. The product or substance may be a medicament or therapeutic substance, for example, a growth hormone, insulin, etc. In some preferred embodiments, an injection device in accordance with the present invention comprises an automatic dispensing system and an energy source, for example, a drive spring, which supplies energy for a dispensing operation. In some preferred embodiments, the present invention relates to a brake mechanism for decelerating a moving part of an injection device for administering a product or substance.

In injection devices known from the prior art in which an output element acting on a product container is driven by a spring, allowance is specifically made for inserting a product container when determining how the device operates. Since the product has to flow through a narrow passage during the dispensing operation, such as a needle, a damping effect is generated due to the viscosity of the product which opposes the force of the output element so that the output element remains at a relatively low speed level. The relatively low speed level results in relatively low impulses or impacts when one moving part or component hits another part or component in the injection device, which has a positive effect on the service life of the device. However, this is only true if a product container has been inserted in the device. If a user initiates a product dispensing operation without inserting a product container, for example, there is no damping effect. This can lead to extreme acceleration values in the mechanism of the injection device, causing very high impulses or impacts when parts make contact with one another, which has a negative effect on the service life of the device. As a result, the device may be so severely damaged that it can no longer be used to administer injections. Increasing the dimensions accordingly, e.g. to absorb or counter impacts on or between moving parts, would increase the size of the device, making it seem clumsy.

Furthermore, a situation can arise in which, when a new ampoule is inserted, the output element does not contact with the plunger. This will be the case if, for example, the output element is pushed too far back during the process of changing the ampoule or if an ampoule which is only partially full is inserted. In this situation, too, extreme acceleration values can occur during the idle stroke of the output element, e.g. the portion of the stroke effected by the output element until it makes contact with the plunger of the ampoule. If a needle is not fitted on the ampoule in such a situation, the product in the ampoule is compressed due to the impact of the output element, causing an increase in pressure, potentially causing the product to be dispensed in an uncontrolled manner when a needle is fitted on the injection device.

SUMMARY

An object of the present invention is to provide an injection device having a structural and/or operational feature which helps prevent the device from being damaged.

Another object of the present invention is to provide an injection device, e.g. an automatic injector, having a structural and/or operational feature or features which help prevent the device from being damaged if it is operated before a product container has been inserted or if a partially empty product container is inserted.

In one embodiment, the present invention relates to a brake mechanism which can be integrated with or in an injection device. The brake mechanism acts on a part or component of the injection device which moves. The movement may be a linear or rotational movement; in some preferred embodiments, the movement is a rotating movement. In some embodiments, the brake operates on the principle of a mechanical movement being converted or dissipated to a different physical variable, e.g. heat.

In some preferred embodiments, a brake mechanism in accordance with the present invention damps the mechanical movement. In a known manner, damping depends on speed. In other words, at a high speed, the damping effect is high and at a low speed, the damping effect is correspondingly low. In the case of a brake mechanism in accordance with the present invention, the maximum rotation speed or angular velocity of a part which rotates quickly during a dispensing operation is limited, e.g. a display barrel or transmission element which transmits energy from an energy storage means, such as a dispensing spring, to an output element, which then acts on a plunger of a product container for the dispensing operation. When a product container is inserted, the parts of the transmission element move relatively slowly due to the damping effect of a liquid contained in the product container. However, at most a negligible degree of damping or braking effect is generated by the brake mechanism. If no product container has been inserted, there is no product container with contents to generate the damping effect so that the parts of the transmission element driven by the dispensing spring are accelerated to a higher speed than would be the case if a product container had been inserted, which means that the damping or braking associated with the brake mechanism increases to a no longer negligible value.

In some preferred embodiments of the present invention, a brake mechanism in accordance with the invention is designed as a module, which can be readily adapted to fit in or be coupled to an injection device.

In accordance with the present invention, a brake device or brake mechanism for an injection device designed to apply a braking action on a moving part of the injection device may generate a braking force which is of a magnitude such that it does not prevent or severely impair a normal dispensing movement of a rotating or moving part but nevertheless prevents or decelerates too rapid a rotation or too high an acceleration or movement of the part. In some preferred embodiments, a brake mechanism in accordance with the present invention generates a braking action on a part which moves or rotates to administer or dispense a dose and is directly connected to or alternatively coupled with the part effecting the dispensing movement, such as a threaded rod or plunger rod, thereby preventing too fast a rotation of the threaded rod or too fast a movement of the plunger rod, such as may otherwise occur during empty operation.

In some embodiments, it is also possible for the brake mechanism not to act directly on the part actively causing the dispensing movement, such as a threaded rod or plunger rod, but to act on or also act on a part coupled with it, for example a part of a transmission element or a drive train, a display barrel, a threaded sleeve, a drive shaft or a brake shoe.

In one embodiment, the brake mechanism comprises a first brake element, for example a brake disc, which can generate a braking force by co-operating with at least a second brake element, for example an element in contact with the brake disc, when the first brake element is moving or rotating. This being the case, the brake element may move in contact with a complementary element, for example, thereby producing the desired deceleration in the form of a friction brake in a known manner. This being the case, the energy of the rotation or movement is converted to heat.

Another possible alternative is for the first brake element to have a profile, such as a toothed profile, on a front face of one or two oppositely lying sides of the brake disc. These teeth of the brake disc may mesh in one or two sets of complementary teeth or complementary profiles disposed opposite one another, e.g. spaced at a fixed distance apart, and a gap is provided between the complementary teeth and an abutting surface or between two sets of complementary teeth so that the brake disc disposed between the complementary teeth and the abutting surface oscillates between the two sets of complementary teeth. In other words, the disc is able to move backward and forward when there is a relative rotation between the brake disc and the complementary teeth or sets of complementary teeth. In this respect, both the brake disc and one or both sets of complementary teeth, which may be coupled or connected by a threaded rod, may be provided as rotating parts. In some preferred embodiments, either the brake disc or the complementary elements are mounted to be rotationally locked or axial displaceable in the direction of the mid-axis of the brake disc, for example.

In the case of another alternative embodiment, the brake may also be provided in the form of a centrifugal brake, in which case one or more solid elements may be provided on a rotating part or coupled with a rotating part which may be biased radially inwardly by the force of a spring, for example. When the part is set in motion during a dispensing operation, the solid elements move outward against the spring force acting radially inwardly and are able to move into contact with at least one and, in some preferred embodiments, several regions of a complementary element, such as a sleeve, during the course of their rotation and may also lie continuously against the complementary element in the position to which they are pushed outward by the centrifugal force, thereby generating the desired deceleration due to friction. This being the case, a brake element such as a rubber facing or some other appropriate coating may be applied to the external face of the solid elements to increase the braking action. Another option is to fit permanent magnets, by which the adhesion between the solid elements and a magnetic or ferromagnetic external enclosure serve as a means of increasing the braking action.

In another embodiment, a brake mechanism in accordance with the present invention may be provided in the form of an eddy current brake, as described herein below with reference to FIG. 6.

In another alternative, a brake mechanism in accordance with the present invention may be provided in the form of a fluidic brake, in which case an element in a volume filled with a fluid and connected to the rotating or moving part moves to generate the desired braking or opposing force due to the movement of the element in the fluid.

BRIEF DESCRIPTION OF THE DRAWINGS

FIG. 6 is a perspective view of an output element with a flange and spring element, FIG. 12 is a perspective view of a brake mechanism of another embodiment of the present invention which operates on the principle of a centrifugal brake.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
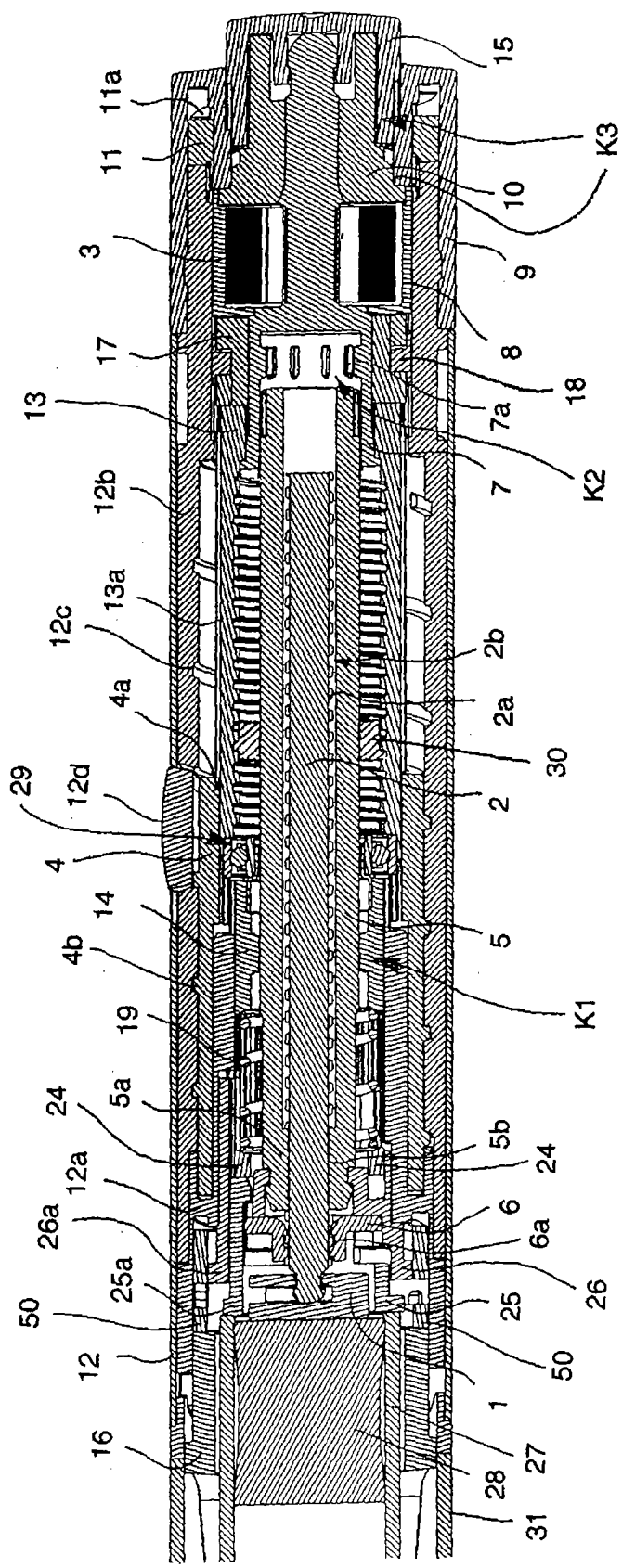
FIG. 1 is a cross-sectional view illustrating a proximal (rear) part of an injection device in accordance with the present invention.

The injection device illustrated in FIG. 1 comprises a drive unit, which, in some embodiments, can be used more than once, and a product container 27 connected to it, which is accommodated in a sleeve-shaped product container holder 16 which can be used multiple times, for example, and which can be secured to the drive unit with the aid of the product container holder 16. The product container 27 can be removed from the injection device after it is empty, disposed of and replaced with a new one. With a view to simplifying the manufacturing and assembly processes, the housing 12 is of a multi-part design with elements 12a, 12b connected to or inserted in it, although in principle, the housing could also comprise a single part. The product container 16 is attached to the drive unit by a bayonet fitting, which is formed by the housing 12, product container holder 16 and sleeve 50. The product container holder 16 is covered by a cap 31, which is fitted on the housing 12, and can be removed in preparation for using the injection device and then fitted back on it.

Figure 4:
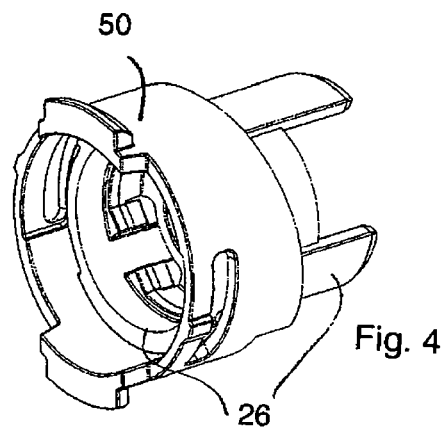
FIG. 4 is a perspective view of the bayonet sleeve illustrated in FIG. 3 with a locating element inserted in it.
Figure 5:
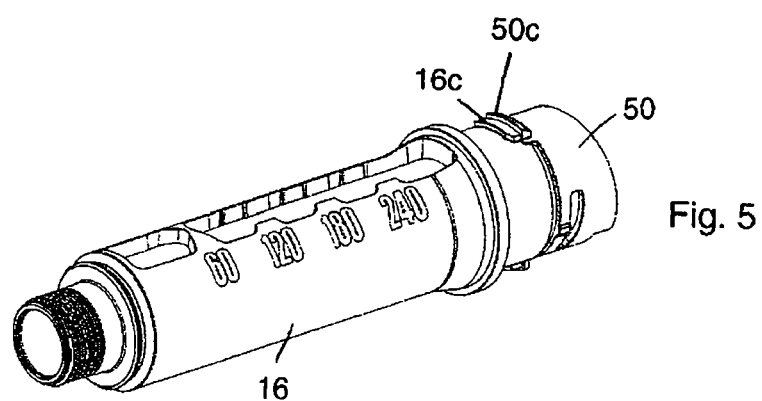
FIG. 5 is a perspective view of a bayonet sleeve and a product container holder, which is moved axially into a fixed torque-transmitting engagement.

FIGS. 2 to 5 illustrate elements of the fixing device provided in the exemplary form of a bayonet fitting. The product container holder 16 has a cam 16c extending radially outwardly and at its proximal (rear) end face is designed so that it can be connected in a positive fit, i.e. in a fixed torque-transmitting fit, to the distal (forward) end face of the sleeve 50, as illustrated in FIG. 5 where housing part 12a has been omitted for illustration purposes. The sleeve 50 has at least one cam 50c extending radially outwardly, which forms a part of a cam 16c, 50c for the fixing device. The cam 50c locates or is positioned in a guide track 12e formed in the housing 12, e.g. in housing part 12a, which has at least one inclined surface 12g. When the sleeve 50 is moved in rotation, the sleeve 50 moves axially relative to the housing part 12a as well as moving in rotation, due to the locating cam 50c. As will be described below, the axial movement of the sleeve 50 results in various advantageous effects.

Figure 2:
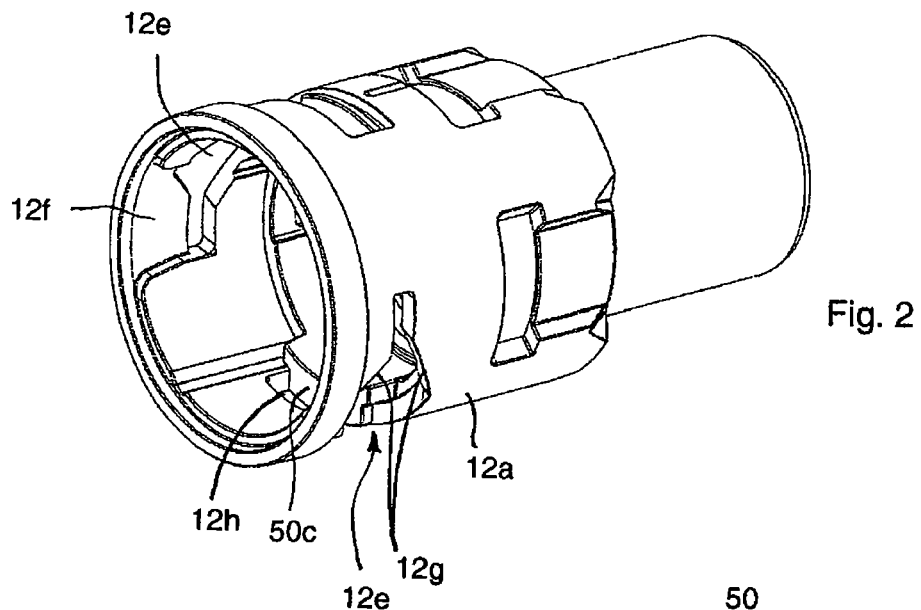
FIG. 2 is a perspective view of a housing part with a guide track for a bayonet fitting with a bayonet sleeve inserted.
Figure 3:
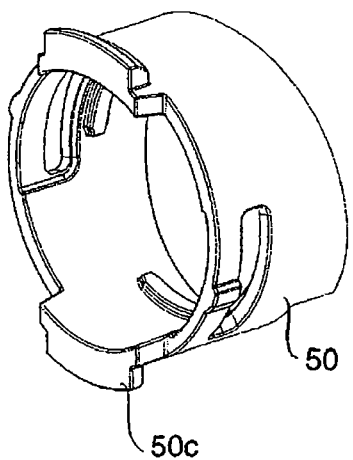
FIG. 3 is a perspective view of the bayonet sleeve illustrated in FIG. 2.

To fit the product container 27 on the drive unit, it may be introduced into the product container holder 16 via the proximal end. The product container holder 16 is then snap-fitted onto the sleeve 50 by an axial movement resulting in a fixed torque-transmitting fit (FIG. 5), so that the cams 16c are inserted through the opening 12f (FIG. 2) into the guide track 12e. FIG. 2 illustrates the bayonet fitting in a locked state without the product container holder 16. In an unlocked state in which the cams 50c are disposed in the region of, and axially flush with the openings 12f, the product container holder 16 can be push-fitted. The cams 16c and 50c then lie one against the other and form a common cam (FIG. 5). A rotation of the product container holder 16 causes the sleeve 50 to be driven. Due to the inclined faces 12g, the sleeve 50 and the product container holder 16 are also moved axially. At the end of the rotation, i.e. on reaching the locked position, the common cam (comprising cam elements 16c, 50c) is disposed in the region 12h of the guide track 12e in which the two cams 16c and 50c are axially clamped together by the sides of the guide track 12e. To this end, the axial width of the guide track in the region 12h is approximately as wide as that of the joint cams 16c, 50c.

As illustrated in FIG. 4, a guide sleeve 26 is accommodated in the sleeve 50, which may also be thought of and/or referred to as the bayonet sleeve. The guide sleeve 26 is connected to the housing 12 so that it can not rotate but can move axially and is connected to the bayonet sleeve 50 so that it can rotate but can not move axially. As a result, when the bayonet sleeve 50 is moved from the unlocked to the locked position and vice versa, the guide sleeve 26 effects a longitudinally guided movement relative to the housing 12.

As may be seen from FIG. 1, a threaded insert 6 is connected and/or latched to the guide sleeve 26 so that it can not rotate or move axially. The threaded insert 6 and guide sleeve 26 may be thought of and/or referred to as a locating element (comprising insert and sleeve elements 6, 26). The threaded insert 6 has an internal thread 6a in which the external thread 2a of an output element 2, which might also be called a plunger rod in this example, is guided so that when the output element 2 is rotated, it is guided by the internal thread 6a of the threaded insert 6 in the proximal direction or in the distal, i.e. opposite, direction, as it is screwed, depending on the direction of rotation.

On its external face, the output element 2 has a thread 2a, which is interrupted by two grooves 2b extending in the axial direction lying opposite one another on the circumference. A coupling sleeve 5 constituting part of a transmission element (comprising elements 7, K2, 5) has two projections 5a, 5b directed radially inwardly lying opposite one another on its distal end which project into the grooves 2b of the output element 2. The coupling sleeve 5 is connected to the locating element so that it can rotate but is not able to move axially. Accordingly, the output element 2 is locked to prevent it from rotating relative to the coupling sleeve 5 but is able to move axially relative to the coupling sleeve 5 when it is rotated relative to the locating element. The coupling sleeve 5 is not able to move axially expect for when the product container 27 is being replaced.

A drive shaft 7 provided at the proximal end of the injection device and forming part of the transmission element has teeth 7a extending radially inwardly which constitute a coupling element of the coupling K2. When operated, i.e. when an operating element 15 is pushed in the distal (forward or injection) direction, the drive shaft 7 and as a result also the teeth 7a are moved in the distal direction, as result of which the teeth 7a locate in the proximal end of the coupling sleeve 5 and establish a fixed torque-transmitting, positive connection.

A spring element or drive spring 3, which may be provided in the form of a helical spring or clock spring, is connected to the housing 12 by one end via a spring sleeve 8 on the external face of the spring element 3. The spring sleeve 8 is prevented from rotating relative to the housing 12 but is able to move axially. At the other end, the drive spring 3 is connected to the drive shaft 7. As a result, energy stored in the spring element 3 can be output as a rotating movement of the drive shaft 7 relative to the housing 12. To dispense a product, the energy of the spring element 3 is transmitted via the transmission element in the form of a rotating movement to the output element so that the latter is screwed relative to the locating element in the distal direction, i.e. in the dispensing direction, and pushes the plunger 28, causing the product to be dispensed from the product container 27.

To set a product dose to be administered, a user can rotate the dose setting element 9 provided in the form of a dose setting button, which is axially fixed relative to the housing 12. The dose setting element 9 is coupled with a coupling element 10 via the coupling K3 so that it is prevented from rotating. The coupling K3 is formed by webs or grooves or teeth of the dose setting button 9, which co-operate in a positive fit with webs or grooves or teeth of the coupling disc 10 to establish a coupling which can be released by a movement of the coupling element 10 in the distal direction. The coupling element 10 can be moved and thus released by operating the operating element 15. When in a state of not being operated, the coupling K3 is held in a coupled state and the coupling K2 in an uncoupled state by a spring element 19, which pushes the drive shaft 7 in the proximal (rear or rearward) direction. During the dose setting operation, the coupling K3 is coupled, i.e. a rotating movement of the dose setting button 9 is transmitted to the coupling element 10. The coupling element 10 is connected to the drive shaft 7 so that it can not move axially and can not rotate and could also be an integral part of the drive shaft 7. The rotating movement of the dose setting element 9 is not transmitted to the coupling sleeve 5 because the coupling K2 is uncoupled.

When the drive shaft 7 is rotated, the drive spring 3 connected to the drive shaft 7 is tensed. To prevent the dose setting button 9 from being turned back due to the drive spring 3 as it is tensed during the setting operation, a ratchet 11 or a ratchet mechanism, which may comprise a ratchet spring 11a, e.g. for clamping retaining elements, may be provided between the housing 12 of the injection device, the components of which might, for example, be a mechanical holder 12a and a mechanical holder 12b and the dose setting button 9. The ratchet mechanism may be designed so that a rotation and/or a tensing of the drive spring 3 is possible in only one direction. In some preferred embodiments, however, the ratchet mechanism is designed so that the rotating action is possible in both directions, e.g. tensing and relaxing of the drive spring 3. Due to the fact of being able to rotate in both directions, a product dose can be both increased and reduced when setting the product dose. A currently set product dose can be read through the window 12d of a display barrel 4.

The rotating movement of the drive shaft 7 is also transmitted to the threaded sleeve 13, which is connected to the drive shaft 7 so that it is not able to move axially or rotate and may also be an integral part of it. The threaded sleeve 13 has at least one groove on its external circumference 13a in which at least one web 4a of the display barrel 4 locates so that a rotating movement of the threaded sleeve 13 is transmitted to the display barrel 4 by the anti-rotation coupling, permitting an axial relative movement between the display barrel 4 and threaded sleeve 13. The display barrel 4 has a thread 4b on its external face which locates in an internal thread 12c of the housing part 12b so that the display barrel 4 is moved due to a rotating movement in the axial direction relative to the housing 12, e.g. in the distal direction. In some preferred embodiments, the display barrel 4 moves in the distal direction of the injection device (towards the left in FIG. 1) during the process of setting and priming the dose by rotating the dose setting button 9. A marking may be provided on the external face of the display barrel 4, such as print, a dose display or a scale, which can be read through an opening or a window 12d in the housing 12b of the injection device, and the marking of the display barrel 4 is moved relative to the window 12d. The display barrel 4 has a rotation stop on its distal end acting in the circumferential direction which moves into an abutting contact with a co-operating complementary stop disposed on the housing part 12a on reaching the maximum dose. The complementary stop is formed by a terminal end of an annular gap of the housing part 12a. An advantage of using a stop which acts in the circumferential direction rather than an axial stop is that the forces acting on the stop are weaker. The display barrel 4 also has another rotation stop on its proximal end acting in the circumferential direction, which moves into an abutting contact with a co-operating complementary stop on the housing 12b on reaching a minimum dose. The complementary stop is formed by the proximal end of the thread 12c.

Figure 14:
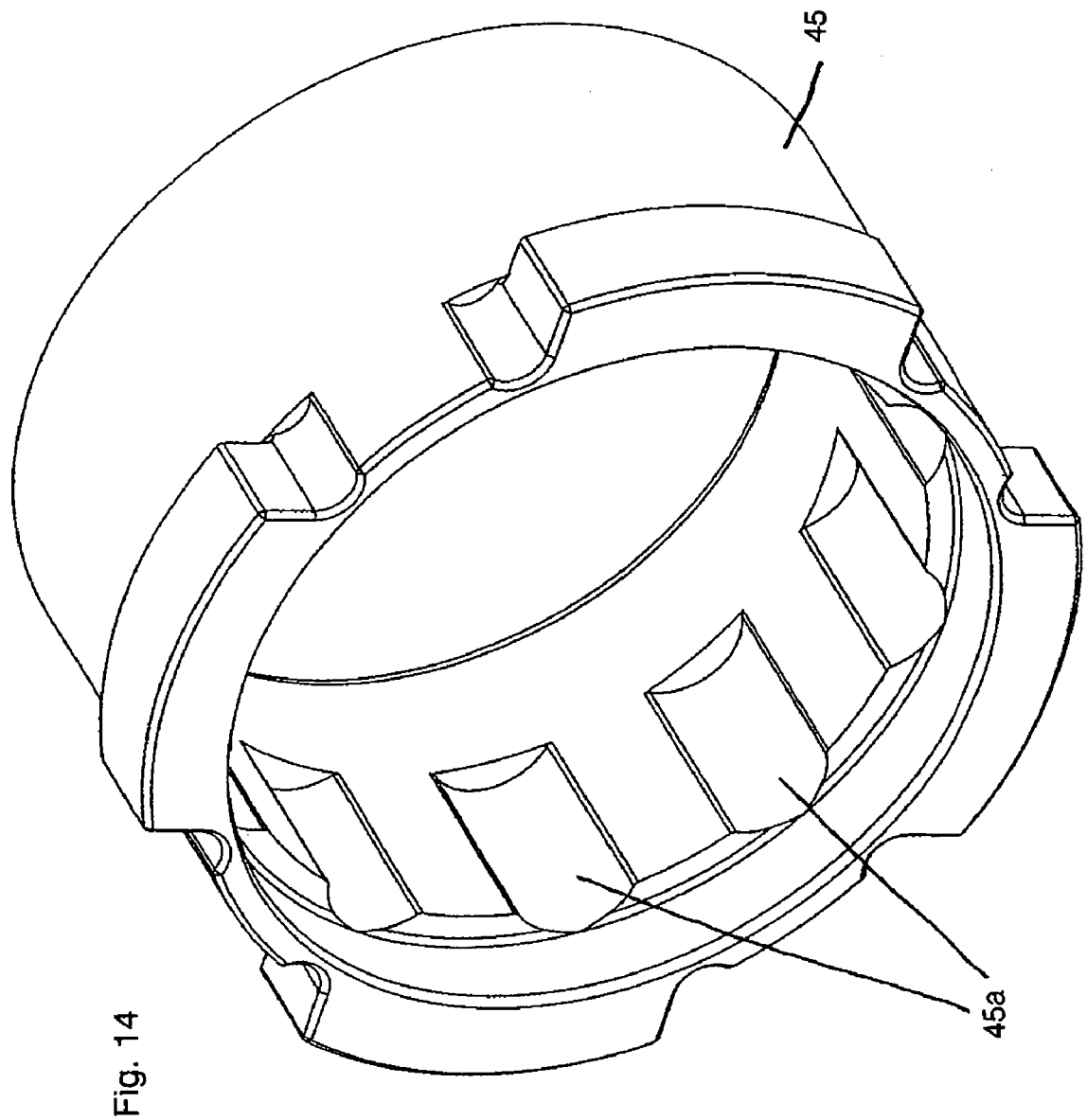
FIG. 14 is a perspective view of a brake housing from FIG. 13.

Once the dose has been set and the drive spring 3 primed by rotating the dose setting button 9, the setting operation is complete. I may be preferable if the dose is primed as the spring 3 is tensed. To correct or adjust the dose, the dose setting button 9 simply has to be rotated in the opposite direction, e.g. to reduce a dose which might have been set too high. In some embodiments, the ratchet 11 may be designed as illustrated in FIGS. 14 and 15 of patent application PCT/CH2007/000243 and/or US Publication 2009/0254035, the teachings of which are incorporated herein by reference.

During the dispensing process, which is triggered by depressing the push button 15, the display barrel 4 is rotated back in the opposite direction and is moved back in the proximal direction due to the thread engagement with the internal thread 12c of the injection device (to the right in FIG. 1). As this happens, it reaches a stop of the display barrel 4 acting in the circumferential direction on the housing of the injection device, e.g. on the housing part 12b. In an unbraked dispensing movement in which the threaded rod 2 is moved in the distal direction without any opposing force, e.g. when no product container has been inserted, this operation may result in too high a strain and, in an extreme situation, deformation or even damage to the display barrel 4 or co-operating part 12b. A brake mechanism (e.g. comprising brake elements, e.g. shoe halves and disc 17, 18) acting on the driving movement is therefore provided, which will be described below.

The coupling K1, comprising the coupling element acting as a lock sleeve 14 and the coupling sleeve 5, is used to couple the coupling sleeve 5 with the housing 12 so that it can not rotate in specific operating modes or to release it to permit a rotation relative to the housing 12. The coupling K1 is uncoupled when the product container 27 is being replaced to enable the output element 2 to be pushed back or screwed in the proximal direction again and to enable the output element 2 to be screwed in the distal direction while product is being dispensed. The coupling K1 is coupled when the product container is attached to the drive unit and the operating element 15 is not being operated. The coupling K1 is provided in the form of teeth on the external face of the coupling sleeve 5, which mesh in teeth on the internal face of the lock sleeve 14. As a result, the coupling sleeve 5 is prevented from rotating relative to the lock sleeve 14. The lock sleeve 14 is mounted in the injection device so that it can not rotate but can move axially relative to the housing 12 and the coupling sleeve 5.

During a dispensing operation, the threaded sleeve 13 is moved in the distal (forward or injection or delivery) direction by operating the operating element 15. As this happens, the threaded sleeve 13 pushes on the bearing 29, which is provided in the form of a ball bearing in this example but may also be a simple slide bearing, so that the bearing 29 pushes against the lock sleeve 14, thereby moving it in the distal direction for a dispensing operation, and holds it in a distal position during a dispensing operation. The coupling element 14 is therefore disposed distally of the projections of the coupling sleeve 5 for the coupling K1. As a result, the coupling K1 remains uncoupled for the duration of the dispensing operation.

When the operating element 15 is operated, the couplings K1, K2 and K3 operate as follows. By depressing the push button 15 seated on the coupling element 10 and/or drive shaft 7, the coupling element 10 is pushed in the distal direction together with the push button 15 and the drive shaft 7. As a result, the coupling K2 is coupled so that the drive shaft 7 is prevented from rotating relative to the coupling sleeve 5. The coupling K1 is then uncoupled due to the movement of the lock sleeve 14, against which the threaded sleeve 13 connected to the drive shaft 7 pushes via the axially displaceable bearing 29. Alternatively, the couplings K1 and K2 may be connected in the reverse sequence.

Once K2 is coupled and K1 is uncoupled, the coupling K3 is also uncoupled due to the movement of the coupling element 10 relative to the dose setting button 9. The coupling element 10, which is connected to the drive shaft 7, is able to rotate relative to the housing 12 once the coupling K3 is uncoupled. The energy or force stored in the drive spring 3 during priming can be transmitted to the drive shaft 7. Accordingly, a torque is applied to the drive shaft 7, which is transmitted by the coupled coupling K2 to the coupling sleeve 5, which rotates in unison with the drive shaft 7 and transmits this rotating movement to the output element 2, which is coupled with the coupling sleeve 5 so that it can not rotate. The output element 2, provided in the form of a threaded rod in this example, converts the rotating movement into an axial movement in the distal direction due to the thread engagement 2a, 6a with the locating element 6, 26, so that the flange 1 provided on the distal end of the threaded rod 2, which may also be construed as part of the output element, is moved in the distal direction of the injection device.

Since, during the product dispensing operation, the threaded sleeve 13 moves in the direction opposite that in which it moves during priming, the display barrel 4 likewise moves in the direction opposite that of the priming operation.

In the normal situation, i.e. when a pre-set product dose has been fully dispensed, the dispensing operation and the movement of the output element 2 in the distal direction continues until the display barrel 4 makes contact with the above-mentioned stop acting in the circumferential direction. In some embodiments, this happens when the value which can be read through the window 12d has been rotated back to 0.

In the situation in which the user of the device releases the operating element 15 as the product is being dispensed, the couplings couple in the order which is the reverse of that in which they uncoupled or coupled during operation. The product dispensing operation is interrupted, as a result of which the value may be seen through the window 12d represents the amount still to be dispensed had the pre-set dose been fully dispensed. The product dispensing operation can be continued by depressing the operating element 15 again, and dispensing can be stopped again by releasing the operating element 15 or the user can wait until the product has been fully dispensed.

In the situation in which the product container contains less product than the maximum dose indicated on the display barrel, the injection device based on this example has an additional device for limiting the maximum dose which can be set for the last time, to prevent the possibility of a bigger product dose being set than that which is still in the container. To this end, a traveler 30 is provided, which at least partially surrounds the coupling sleeve 5 and locates with the coupling sleeve 5 in such a way that the traveler 30 is not able to rotate relative to the coupling sleeve 5 but is able to move axially. The traveler 30 also locates or is positioned by a thread on its external circumference that engages with an internal thread of the threaded sleeve 13. This arrangement causes an axial movement of the traveler 30 when there is a relative rotation between the threaded sleeve 13 and coupling sleeve 5, and when there is no relative rotation the traveler 30 does not effect an axial movement. When setting a product dose, the threaded sleeve 13 turns relative to the coupling sleeve 5 so that the traveler 30 moves in the proximal direction. During dispensing, on the other hand, no relative movement takes place between the coupling sleeve 5 and threaded sleeve 13 due to the coupled engagement of the coupling K2. Accordingly, the traveler does not move. After setting doses and dispensing product several times, the traveler 30 moves into an abutting contact with the drive shaft 7, so that it is no longer possible to increase the dose, even if the display would actually permit this.

The user can replace the product container 27 with a new one. To this end, the product container holder 16 may be removed by rotating the drive unit relative to the housing 12. As the product container 27 is moved from the secured position into the non-secured position, e.g. as the bayonet fitting is released, the locating element is moved together with the output element 2 and the coupling sleeve 5 in the distal direction relative to the housing 12 and to the coupling element 14, thereby releasing the coupling K1. The projections of the coupling sleeve 5 pointing radially outwardly to establish the coupling K1 are now disposed distally of the coupling element 14. The output element 2 can now be screwed into the drive unit with a relatively slight force acting in the proximal direction because the thread of the output element is not retained by friction. As the output element 2 is screwed back, the coupling sleeve 5 is turned relative to the threaded sleeve 13 and so in the direction opposite that during product dispensing, causing the traveler 30 to be pushed back in the distal direction again. The screwing-back operation may take place against the force of a spring element, at least across a part of the total distance, which tries to push the output element in the distal direction, for example. The spring element may act or be disposed between the output element 2 and the drive shaft 7 for example. Other possible spring elements will be described below specifically with reference to FIG. 6. It is generally preferred if the force of such a spring element is weaker than the force needed to produce an interaction via the plunger from the output element 2 onto the product.

Also during the process of removing the product container 27, the retaining element 25 used to secure the product container 27 in the product container holder 16 is pushed in the distal direction by the spring 19 until it makes contact with the locating element 6, 26. This contact prevents the spring 19 from fully relaxing when the product container 27 is removed. This is of advantage because the spring 19 should be able to apply sufficient force to hold the coupling K3 in a coupled engagement even when a product container 27 has been removed.

By virtue of another aspect, a spring-mounted flange may be used, as illustrated in FIG. 6 for example.

After replacing the product container 27, e.g. an ampoule, capped vial or the like, the user is prompted to proceed with priming, as may be described in operating instructions. This is useful on the one hand because there may be air in the product container 27 and on the other hand because the output element 2 may have been previously pushed fully into the drive unit and a certain amount of clearance may have been created between the plunger 28 and the flange 1 due to the different level to which the product container 27 is filled.

FIG. 6 illustrates an output element 2 with a flange 1 attached to its front or distal end, which is non-displaceably connected to the threaded rod. Disposed between the flange 1 and the threaded insert 6 illustrated in FIG. 6 is a spring element 38, which may be provided in the form of resilient arms 38a extending out at an angle, for example. These resilient arms 38a may be secured to the flange 1 or/and to the threaded insert 6. Another option would be to injection mold a suitable elastomer onto the flange 1 or/and onto the threaded insert 6. After a new product container 27 has been inserted, a clearance may occur between the flange 1 and the plunger 28, which may be attributable to a difference in the level to which product containers 27 have been filled when full, given that they have a certain tolerance.

After pushing in the flange 1 connected to the threaded rod 2, the flange 1 based on the embodiment illustrated in FIG. 1 lies directly against the threaded insert 6.

In the embodiment illustrated in FIG. 6, the at least one spring element 38 has pushed the flange 1 away from the threaded insert 6 in the distal direction by a predefined distance. This means that when a product container 27 has been inserted or while a product container 27 is being inserted, the flange 1 will move into contact with the proximal end of the plunger 28, even if the plunger 28 is pushed into the product container 27 by differing distances caused by manufacturing tolerances of different product containers. Conventional means for eliminating the clearance between the flange 1 and plunger 28 are therefore no longer absolutely necessary and may even be dispensed with, for example.

As may be seen from FIG. 1, the injection device, e.g. the drive unit, comprises a brake (which may be thought of as comprising brake elements or components 17, 18) which decelerates a rotating part, in this example the transmission element or/and the driving movement. If conventional injection devices are used incorrectly, i.e. if no product container has been inserted, but the device is nevertheless operated, there is a risk of placing too high a strain on or even damaging the components of the injection device. When a product container 27 is inserted, the forces and movements which occur are damped by the viscosity of the product during the product dispensing operation. In the absence of a product container, there is no such damping effect. It is the brake in accordance with the present invention which is used for this purpose, thereby preventing excessive strain.

Figure 7A:
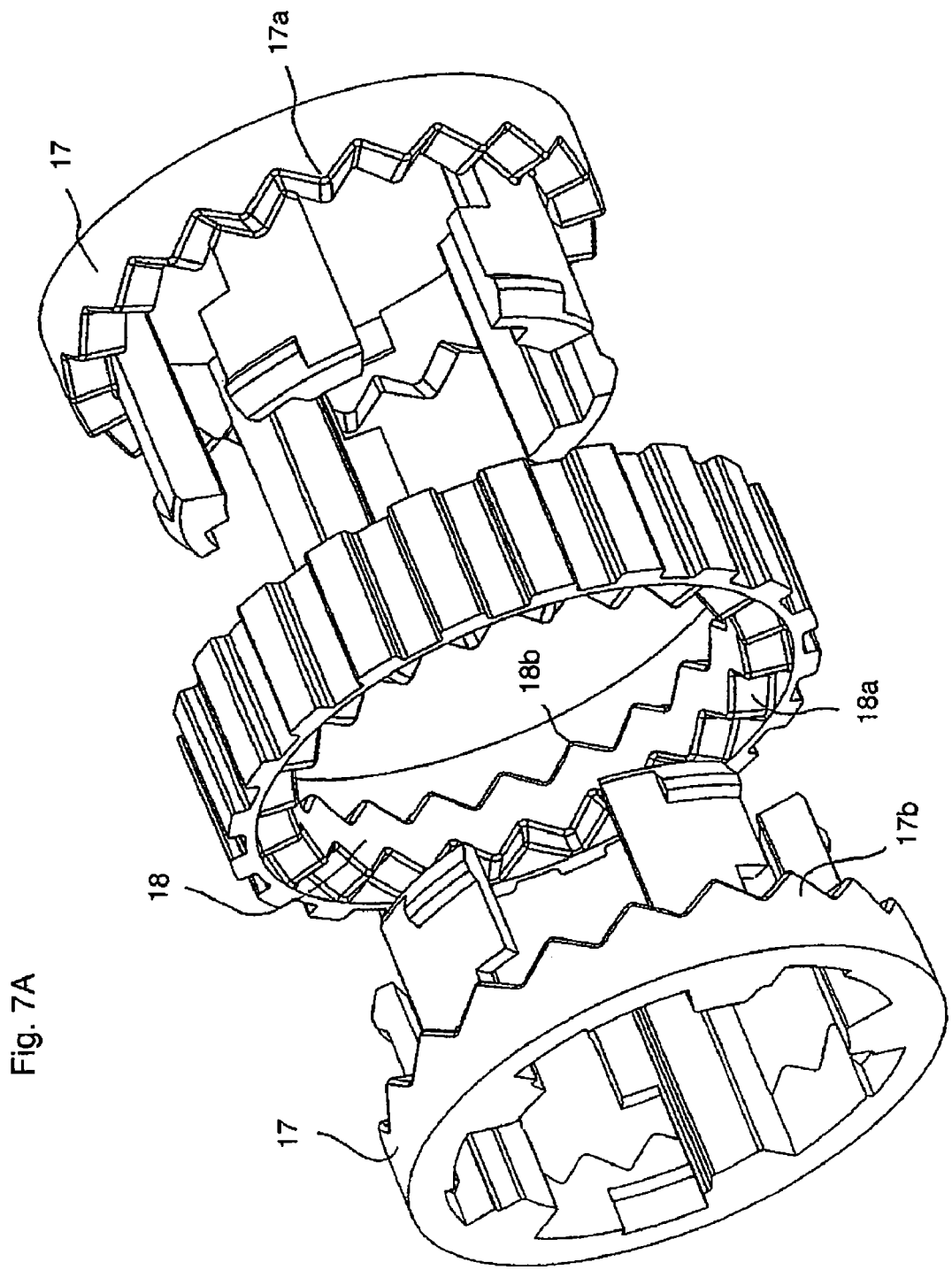
FIGS. 7A and 7B are an exploded view and a perspective view of one embodiment of a brake mechanism in accordance with the present invention.
Figure 7B:
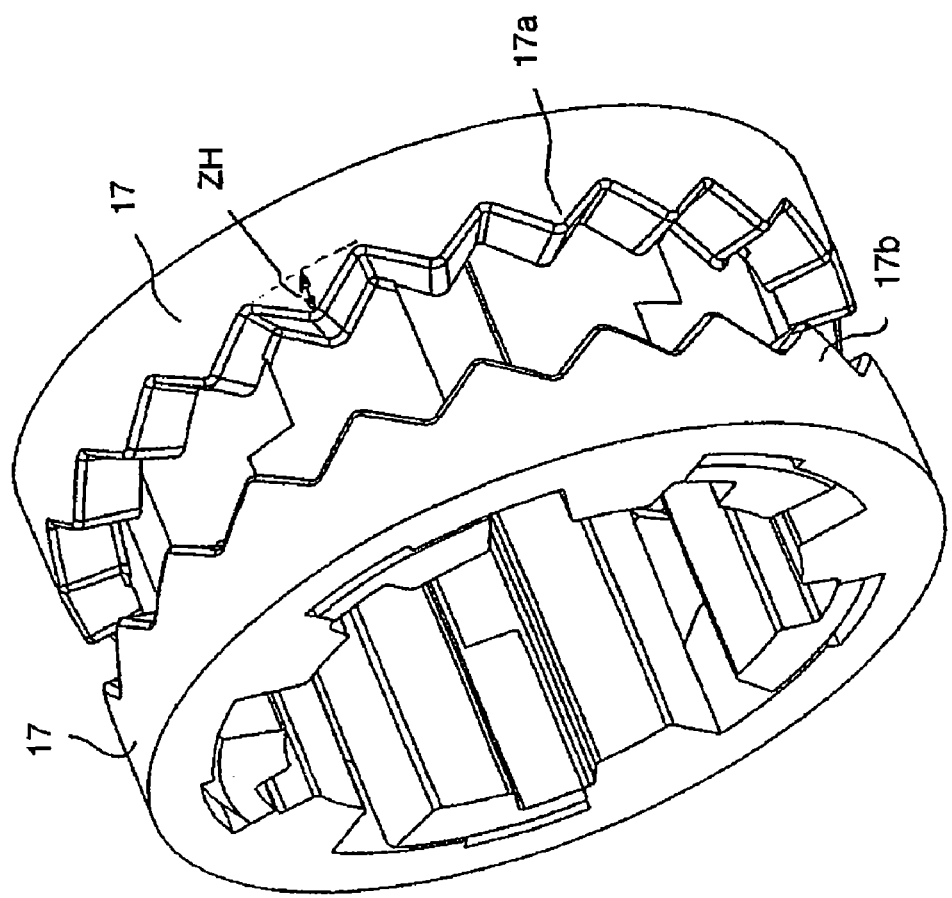
Figure 8:
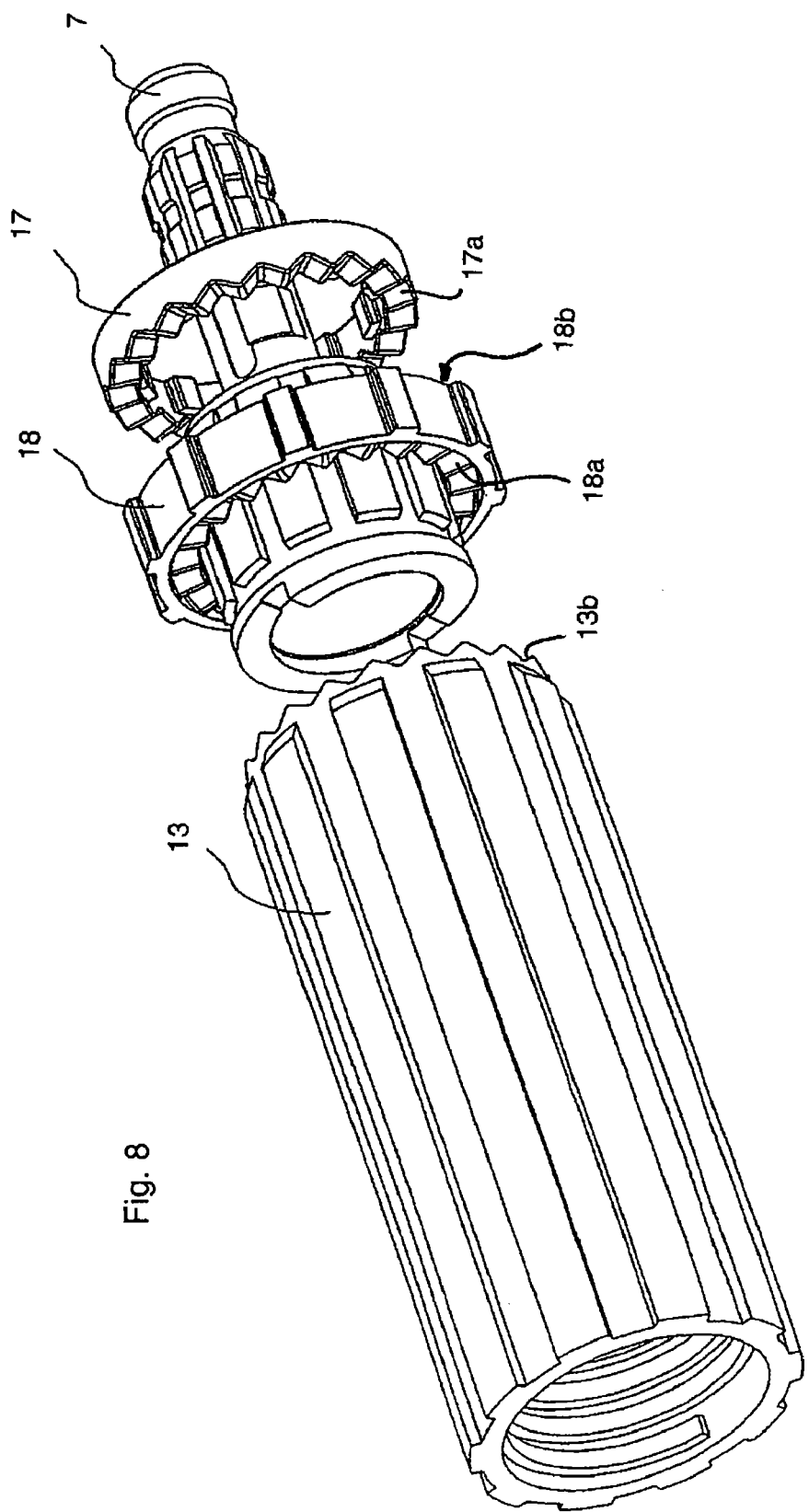
FIG. 8 is a perspective exploded view of another embodiment of a brake mechanism in accordance with the present invention.

FIGS. 7A, 7B and 8 are diagrams on a larger scale illustrating embodiments of a brake mechanism suitable for the device illustrated in FIG. 1, e.g. a first and second embodiment, respectively, each of which operates in a similar manner. The first embodiment illustrated in FIGS. 7A, 7B has two brake shoe halves 17 latched to one another so that they can not rotate and so that they can also not move axially, which have profiled portions directed toward one another, between which an annular gap is formed in which a brake disc 18 is accommodated. The annular gap is of a defined width and, in an alternative arrangement, the brake shoe halves could move axially relative to one another. The brake shoe 17 could be of an integral design. The brake disc 18 is accommodated so that it can not rotate relative to the housing 12 but can move axially, due to the profiled external circumferential surface of the brake disc locating in a profiled inner circumferential surface of the housing part 12b. At least one brake shoe half 17 or the entire brake shoe is mounted at least so that it can not rotate in the drive train or transmission element. The sleeve-shaped brake shoe 17 has projections pointing radially inwardly, which locate in a matching profile of the drive sleeve 7. The brake disc 18 is able to move between the brake shoe halves 17. The brake disc 18 is mounted so that it can not rotate, e.g. is guided in a groove, and so that it is able to move axially in the injection device or housing part 12b. The brake disc 18 is toothed on the top and bottom face with teeth 18a, 18b on the end face projecting circumferentially in both directions and having an identical or different tooth height ZH, and is mounted or displaceably clamped between the threaded sleeve 13 and the brake shoe 17, e.g. with a small clearance of approximately a tooth size or tooth height ZH or bigger, the latter having co-operating complementary teeth 13b respectively 17a, e.g. with a corresponding or identical tooth height ZH.

Due to the fixed torque-transmitting connection between the transmission element (which, again, may be thought of and/or referred to as comprising elements 7, K2, 5) during a dispensing operation or when what may be thought of and/or referred to as "firing blank," i.e. when no product container has been inserted, the brake shoe 17 is moved in rotation relative to the brake disc 18. When this happens, the disposition of the brake shoe teeth 17a, 17b ensure that the brake disc 18 oscillates axially between the threaded sleeve 13 and the brake shoe 17. As a result, the distal teeth 18a and proximal teeth 18b of the brake disc 18 move alternately into contact with the co-operating complementary teeth 17b and 17a. Due to one or more of the resultant friction, elastic deformation and the oscillating mass, a corresponding loss occurs, thereby limiting the maximum angular speed ω of the rotating parts 13 and 17.

The embodiment illustrated in FIG. 8 operates on a similar principle, the difference being that one of the two brake shoe halves and/or its end-face tooth profile is formed by the transmission element or the threaded sleeve 13 connected to the transmission element so that it cannot rotate. A fixed, defined distance may be provided between the profiles 17a and 13b, or alternatively a variable distance, because the brake shoe half 17 is able to move axially relative to the threaded sleeve 13. Due to the spring 19, the profiles 13b and 17a can be pushed toward one another so that they move into a meshing contact with the profiles 18a and 18b.

Figure 9:
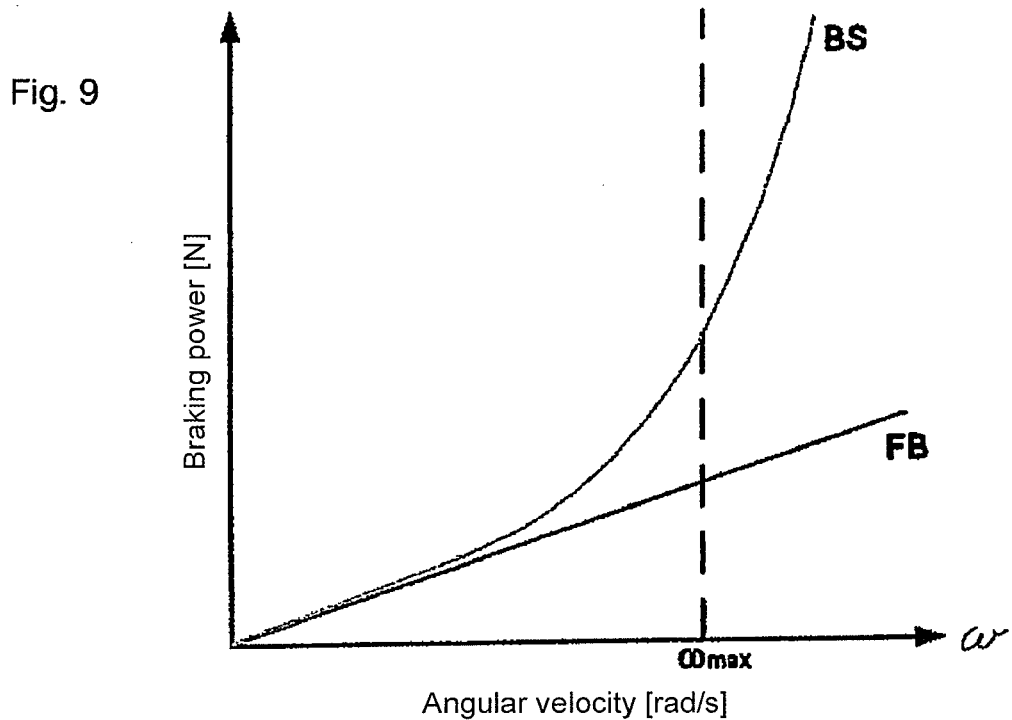
FIG. 9 is a diagram schematically plotting braking force as a function of angular velocity.

Due to the vibration or oscillation of the brake disc 18 between the threaded sleeve 13 and brake shoe 18 which increases with the angular velocity w, the braking force increases disproportionately as the angular velocity ω increases, so that the curve BS of braking forces schematically illustrated in FIG. 9 can be achieved.

FIG. 9 is a schematic illustration plotting the curve of the braking force which can be achieved by a brake mechanism in accordance with the present invention, from which it may be seen that the braking force rises to an increasing degree with the angular or rotational velocity ω. In some preferred embodiments, the braking force is relatively low or zero up to the maximum permissible angular velocity $\omega_{max}$ and rises sharply with effect from the maximum permissible angular velocity $\omega_{max}$.

Figure 10:
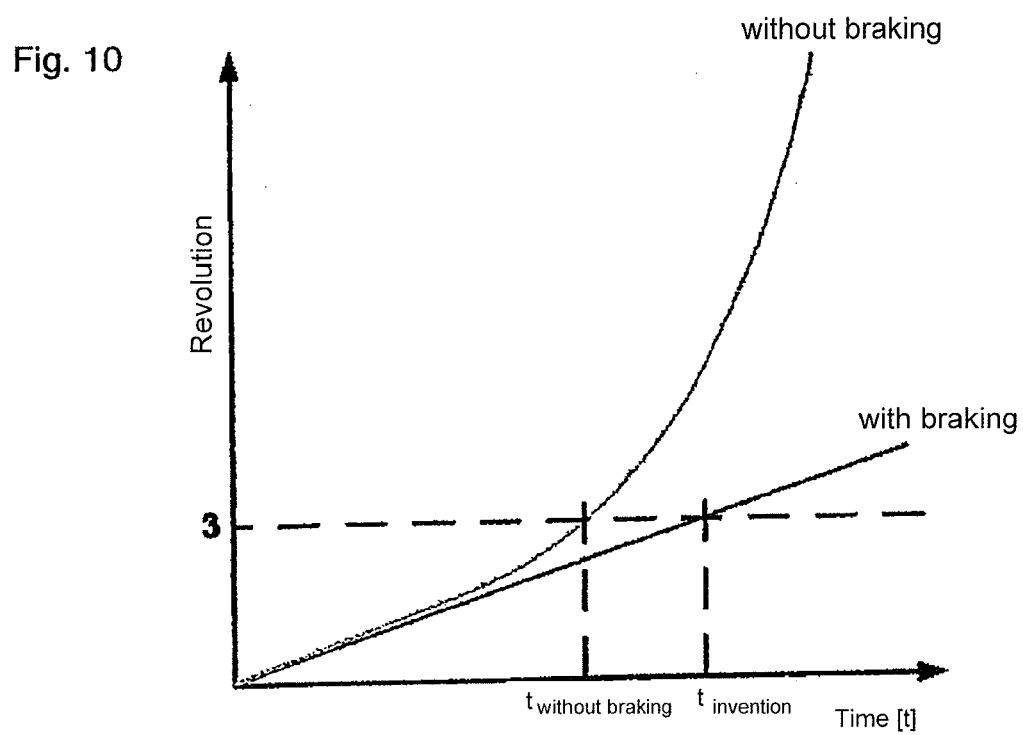
FIG. 10 is a diagram explaining braking action as a function of time.

FIG. 10 illustrates the angle of rotation of the display barrel 4 as a function of time, which is able to effect three full revolutions (3×360°) in the embodiments illustrated as an example. As may be seen from FIG. 10, the display barrel 4 has completed three full revolutions after the time $t_{non-braked}$, which is shorter than the time $t_{invention}$ in the case of a decelerated rotating movement of the display barrel 4 during which the angle of rotation increases linearly as a function of time.

Due to the braking force generated by the oscillating brake disc 18, the maximum possible angular velocity $\omega_{max}$ of a dispensing movement can be reduced or limited so that the backward-rotating display barrel 4 is able to move into an abutting contact with the stop acting in the circumferential direction or the housing part 12b at only a maximum speed predefined by the brake. If the brake is designed accordingly, the maximum possible contact speed of the display barrel 4 is so low that there is little chance of deformation or damage occurring due to the impact. Other brake mechanisms may also be used as an alternative to a brake disc 18 oscillating between the threaded sleeve 13 and brake shoe 17.

For example, as an alternative or in addition, the brake may be based on another embodiment in the form of a centrifugal brake as illustrated in FIG. 12. In this case outwardly displaceable brake shoes 41 are mounted on the transmission element or/and the drive shaft 7 and/or another part which rotates with the drive shaft 7, for example the coupling element 10, the threaded sleeve 13 or the display barrel 4, which have a mass and which effect the same rotation as the rotating part. The brake shoes 41 may, but need not necessarily, be inwardly or outwardly biased by a spring. The brake shoes may be pivoted or moved radially outwardly by the centrifugal force to move into a braking engagement with a sleeve 42, for example the housing 12. In this embodiment, pins 40 or fasteners extending radially outwardly are provided, the ends of which are provided with brake pads 41 biased by the spring, for example. When the rotation speed of the non-braked or only partially braked rotating element is sufficiently high, the brake pads 41 are moved radially outwardly by the centrifugal force, optionally also assisted by the spring-biased support, and can move into contact with an outer static sleeve 42, thereby producing the desired braking effect due to friction. The outer static sleeve may also be formed by the housing 12 or housing part 12b.

Figure 11A:
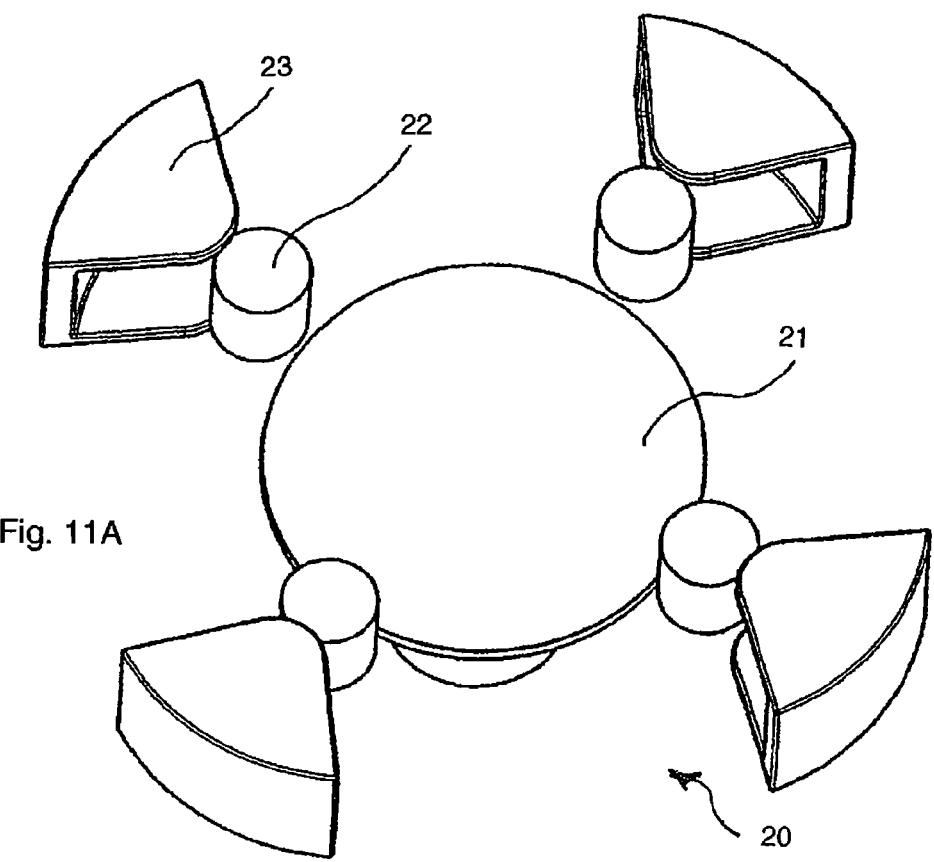
FIGS. 11A and 11B are an exploded view and a perspective view of another embodiment of a brake mechanism in accordance with the present invention which operates on the principle of an eddy current brake.
Figure 11B:
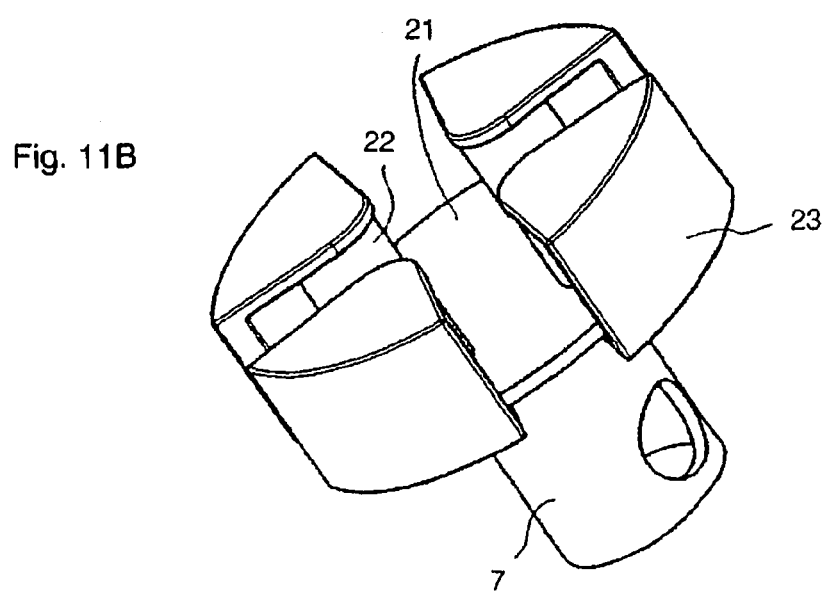

In another embodiment illustrated in FIGS. 11A and 11B, the brake may be provided in the form of an eddy current brake 20, in which case a brake disc 21 may be connected to a rotating part which has to be decelerated, for example the transmission element, drive shaft 7, threaded sleeve 13 or display barrel 4, and the elements interacting with the brake disc may be connected to the housing or an element fixedly disposed on the housing or to an element rotating relative to the brake disc.

In some preferred embodiments, the brake disc 21 is made from a good electrical conductor, such as pure aluminium or copper, for example. Rare earth alloys may be used as the material for the axially magnetised magnets 22, neodymium for example. The permanent magnetic field may be linked by a magnet yoke 23 made from iron to the air gap, where it extends through the brake disc 21 as vertically as possible. The braking force is created by the surface and flow density in the air gap and the rated current in the brake disc 21, for which purpose the surface should be as large as possible, the air gap should be as small as possible and the disc thickness should be as big as possible. The braking torque occurs over the averaged radius (working radius). Brakes may be designed with several magnet systems which act on a disc 21.

The usual approximation calculations are used to calculate the current density, braking power and hence braking torque of an eddy current brake. Leaving aside the effect of the air gap, it is assumed that there will be a standard cylindrical magnetic flow and it is stipulated as a condition that the pole diameter should be sufficiently small compared with the radius of the disc 21. At high speeds, the approximation is inaccurate, among other reasons because the magnetic fields caused by the eddy currents cause a not inconsiderable feedback and hence non-linearity.

In some preferred embodiments, the magnets 22 and the magnet yoke 23 are connected to the housing 12 of the injection device or the housing part 12b or another non-rotating part to be able to generate the desired eddy current braking effect of the brake disc 21.

Figure 13:
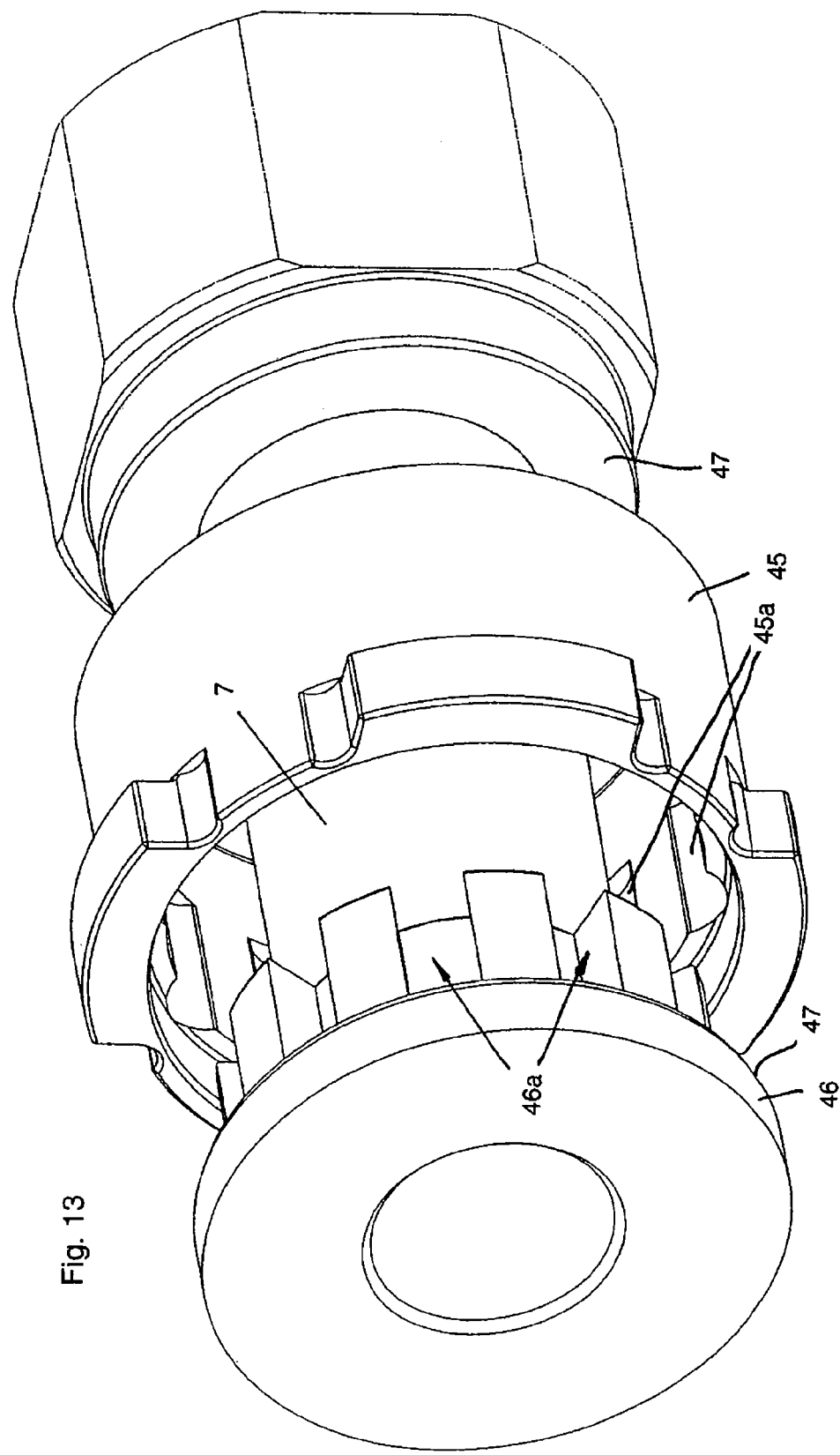
FIG. 13 is an exploded view of a brake mechanism in accordance with another embodiment of the present invention which operates on the principle of a fluidic brake.

In another embodiment illustrated in FIGS. 13 and 14, the brake may be provided in the form of a fluidic or hydrodynamic brake. If a standard fluid is used as the braking medium, the linear braking curve FB indicated in FIG. 4 can be obtained for the eddy current brake. However, if the intention is to achieve a braking force which rises more sharply as a function of angular velocity ω, so-called non-Newtonian fluids may be used, as a result of which, unlike a Newtonian fluid, the viscosity does not remain constant but increases when a shearing force acting on the fluid is increased, which is the case as the speed increases. These are what are known as anomalous viscous fluids.

In the case of the fluidic brake, the braking force is generated by two fluid surfaces moving against one another. In particular, the braking force is generated by a fluid volume which is sheared by a relative movement. The shearing stresses which occur during such movements correspond to the braking force. The volume is provided in the form of a chamber split into two parts 45a, 46a, in which the fluid is disposed. One chamber part 46a is disposed in a rotating part 46 and the other chamber 45a is disposed in a part 45 relative to which the rotating part 46 is able to rotate. The part 46 may be connected so as to rotate in unison with the drive shaft 7 or to the transmission element or another part which rotates when product is being dispensed. The part 45 rotates in unison with at least the housing 12 or a stationary part on the housing. Furthermore, the part 45 may be able to move axially or may be axially immobile relative to the housing 12. The sleeve-shaped part 45 may be thought of and/or referred to as a brake housing and the part 46 mounted in the sleeve 45 as a brake shaft. When the brake is in the assembled state, the fluid chamber halves 46a distributed axially around the external circumference of the brake shaft are axially on a level with the fluid chamber halves 45a distributed around the internal circumference of the brake housing. More, the same number or fewer fluid chamber halves 45a may be provided than 46a. In the assembled state, a slim gap is disposed between the internal diameter of the brake housing 45 and the external diameter of the brake shaft 46 in the region of each of the fluid chamber halves 45a, 46a, which may be dimensioned so that fluid is conveyed into the gap or no fluid or virtually no fluid is conveyed into the gap when the brake shaft 46 is rotating relative to the brake housing 45. The brake housing 45 may be axially sealed at both ends with sliding seal elements 47 so that no fluid is able to escape from the brake. The seal elements 47 may be provided in the form of a lid. The lid may be provided as a separate part or serve as the coupling shaft, for example.

Advantages of the present invention include, for example, that the braking force rises as the angular velocity increases, i.e. a movement can take place during product dispensing operations without braking or virtually without braking, and the braking force of a brake in accordance with the present invention does not increase to any significant degree except in the event of the problem situations described above, when, compared to normal or intended dispensing operations, relatively higher rotation speeds and/or impacts may occur.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A brake mechanism for an injection device for generating a damping effect on a rotating part of the injection device, the brake mechanism comprising:
 a brake disc and at least one complementary element by cooperation of which the brake mechanism generates the damping effect on the rotating part, wherein
 the rotating part may rotate at a higher speed and a lower speed, and wherein
 the damping effect is greater at the higher speed than at the lower speed.

2. The brake mechanism as claimed in claim 1, wherein the rotating part is at least one of a threaded rod, a sleeve, a display barrel, a drive shaft, a threaded sleeve, a brake shoe or a part connected to or coupled therewith.

3. The brake mechanism as claimed in claim 1, wherein the brake disc acts as a friction brake in conjunction with the at least one complementary element.

4. The brake mechanism as claimed in claim 1, wherein the brake disc comprises a profile on one side or on both sides and extending partly or completely around the circumference.

5. The brake mechanism as claimed in claim 4, wherein the at least one complementary element of the brake disc comprises a complementary profile.

6. The brake mechanism as claimed in claim 5, comprising more than one complementary element, and the complementary elements are fixedly connected to one another and the complementary profiles are spaced apart from one another by a distance which is the same as or bigger than a profile depth of the profile of the brake disc.

7. The brake mechanism as claimed in claim 1, wherein the brake disc is nonrotatable and axially displaceable and the at least one complementary element is rotatable.

8. The brake mechanism according to claim 1, wherein the rotating part continues to be rotatable whether the damping effect is generated at the higher speed or at the lower speed.

9. A damping mechanism for an injection device for generating a damping effect on a rotating part of the injection device, the damping mechanism comprising a brake disc and at least one complementary element by cooperation of which the damping mechanism generates the damping effect on the rotating part, wherein the brake disc comprises an annular body and wherein the brake disc and the at least one complementary element each comprise a plurality of complementary teeth, each tooth having a tip shaped to ease relative rotation of the brake disc and the at least one complementary element.

10. The damping mechanism according to claim 9, wherein the damping effect does not stop the rotation of the rotating part.

11. The damping mechanism according to claim 9, wherein the tips are flattened.

12. The damping mechanism according to claim 9, wherein the rotating part may rotate at a higher speed and a lower speed, and wherein the damping effect is greater at the higher speed than at the lower speed.

13. The damping mechanism according to claim 12, wherein the injection device receives a cartridge or ampoule, and the damping effect takes place when the cartridge or ampoule is not received in the injection device.

14. A damping mechanism for an injection device for generating a damping effect on a rotating part of the injection device, the damping mechanism comprising a brake disc and at least one complementary element by cooperation of which the damping mechanism generates the damping effect on the rotating part, wherein the brake disc comprises an annular body and wherein the brake disc and the at least one complementary element each comprise a plurality of complementary teeth, the teeth having a shape to ease relative rotation of the brake disc and the at least one complementary element, the shape comprising a flattened region between each tooth and each tooth having a flattened tip.

* * * * *